United States Patent
Guy et al.

[19]

[11] Patent Number: 5,935,119
[45] Date of Patent: Aug. 10, 1999

[54] PERFUSION STRUCTURE

[75] Inventors: Thomas D. Guy, Hobe Sound, Fla.; Kenneth E. Toso, Wilton, Conn.

[73] Assignee: United States Surgical Corporation, Norwalk, Conn.

[21] Appl. No.: 08/915,505

[22] Filed: Aug. 6, 1997

[51] Int. Cl.⁶ .................................................. A61M 25/00
[52] U.S. Cl. .................... 604/500; 604/523; 604/532; 606/185
[58] Field of Search ................ 604/49, 51, 53, 604/164, 165, 175, 264, 500, 523, 532; 606/108, 185, 194, 195, 198

[56] References Cited

U.S. PATENT DOCUMENTS

| | | |
|---|---|---|
| 4,461,305 | 7/1984 | Cibley . |
| 4,469,098 | 9/1984 | Davi . |
| 4,658,817 | 4/1987 | Hardy . |
| 4,693,244 | 9/1987 | Daikuzono . |
| 4,696,308 | 9/1987 | Meller . |
| 4,798,207 | 1/1989 | Wade ................................. 604/175 X |
| 4,860,743 | 8/1989 | Abela . |
| 4,862,887 | 9/1989 | Weber et al. . |
| 4,940,061 | 7/1990 | Terwilliger et al. . |
| 5,324,300 | 6/1994 | Elias et al. . |
| 5,437,660 | 8/1995 | Johnson et al. . |
| 5,500,012 | 3/1996 | Brucker et al. . |
| 5,511,556 | 4/1996 | DeSantis . |
| 5,575,787 | 11/1996 | Abela et al. . |
| 5,615,690 | 4/1997 | Giurtino et al. . |
| 5,620,439 | 4/1997 | Abela et al. . |
| 5,655,548 | 8/1997 | Nelson et al. ......................... 128/898 |
| 5,672,170 | 9/1997 | Cho et al. . |
| 5,810,836 | 9/1998 | Hussein et al. ......................... 606/108 |

*Primary Examiner*—John D. Yasko

[57] ABSTRACT

The present disclosure is directed to a perfusion stent and method for implanting the same in a TMR channel for perfusing blood to ischemic areas of the head. The stent includes a head and a stem extending perpendicular to the head. The stem includes a cylinder having a plurality of holes. The method comprises the steps of creating the TMR channel, and implanting the perfusion stent within the TMR channel in order for blood within a ventricle to enter the stem and be perfused to the heart muscle.

13 Claims, 4 Drawing Sheets

PERFUSION STRUCTURE

BACKGROUND

1. Technical Field

The present disclosure relates to a perfusion apparatus and method. The structures disclosed are particularly suited for transmyocardial revascularization (TMR).

2. Background of the Related Art

A variety of procedures and apparatus have been developed to treat cardiovascular disease. For example, minimally invasive surgical procedures such as balloon angioplasty and atherectomy have received extensive investigation and are in wide use. In some patients, however, circumstances still require conventional open heart bypass surgery to correct or treat advanced cardiovascular disease. In some circumstances, however, patients may not be suitable candidates for bypass surgery.

An alternative or adjunct procedure to bypass surgery is transmyocardial revascularization (TMR), wherein holes are formed in the heart wall. These holes theoretically provide alternative blood flow channels for ischemic heart tissue and have been attributed to decreased pain (angina) associated with cardiovascular disease. The holes can be created using laser energy. In early laser myocardial revascularization, a $CO_2$ laser was used to produce holes in the heart wall by transmitting laser energy from the laser to the heart wall. Typical $CO_2$ lasers used for transmyocardial revascularization (TMR) are externally located and have an articulated support arm for aiming and directing laser energy through a series of mirrors that reflect the energy onto the heart wall. Thus, some surgical opening of the chest wall is required to access the heart muscle. The entrance wound in the heart can be closed by relatively brief external pressure while the endocardial and myocardial layers remain open to permit blood flow from the ventricle to the heart muscle.

Less traumatic approaches to laser myocardial revascularization have been disclosed. These methods include the use of optical fibers introduced either through a patient's vasculature or, alternatively, directly into the patient's chest cavity. The intravascular method involves the direction of laser energy from inside the heart to form a bore in the heart wall while the other method involves introduction of the lasing apparatus through a relatively small incision in the patient's chest to access the outer wall of the heart.

During a conventional procedure, typically dozens of channels are created from the epicardium, through the myocardium and endocardium and into the ventricle, with each channel being of sufficiently small diameter such that the end portions of the channels at the epicardium can be closed by blood clotting. The channels are preferably created by employing either a mechanical coring apparatus or an advancing lasing device. With either technique, an important objective is to produce channels that remain patent in the long term and which do not close up due to fibrosis and/or scarring. Channel closure can reduce or eliminate the benefits attributable to TMR procedures.

Therefore, there is a need for devices and methods for ensuring that TMR channels remain open to allow oxygen rich blood to reach the desired areas of the myocardium.

SUMMARY

The present disclosure is directed to a perfusion stent and method for implanting the same in a TMR channel for perfusing blood to ischemic areas of the heart. The stent includes a head and a stem extending substantially perpendicular to the head. The stem is preferably cylindrical and includes a foraminous or other pourous structure. The method comprises the steps of creating the TMR channel by an apparatus having a mechanical coring assembly or advancing lasing device, and implanting the perfusion stent within the TMR channel in order for blood within a ventricle to enter the stem portion and be perfused to the heart muscle.

Advantageously, with the presently disclosed apparatus and method, the TMR channel remains patent in the long term and the channel opening is capped by the stent head to inhibit bleeding.

BRIEF DESCRIPTION OF THE DRAWINGS

Various preferred embodiments are described herein with reference to the drawings, wherein.

DETAILED DESCRIPTION

Figure 1:
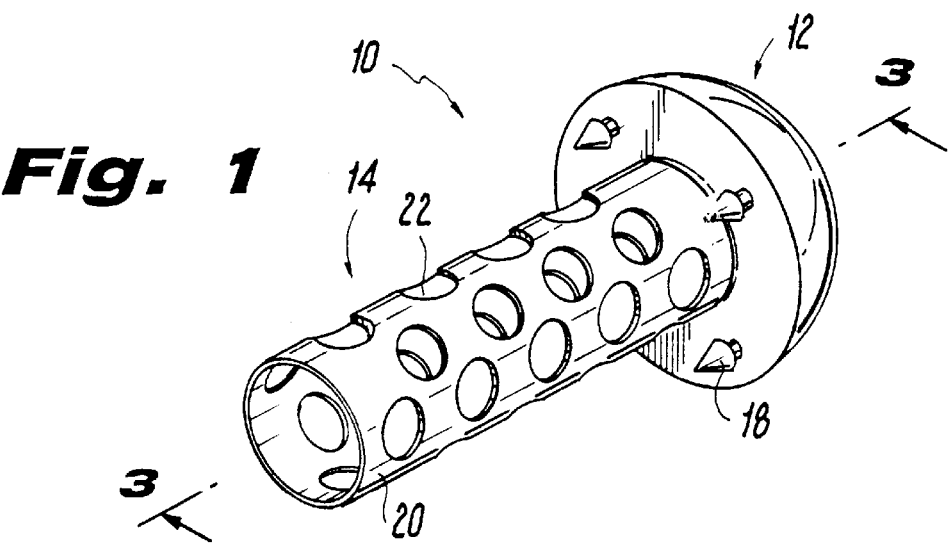
FIG. 1 is a right perspective view of one embodiment of a perfusion stent.

Preferred embodiments of TMR methods and apparatus will now be described in detail with reference to the drawings, in which like reference numerals designate identical or corresponding elements.

Figure 2:
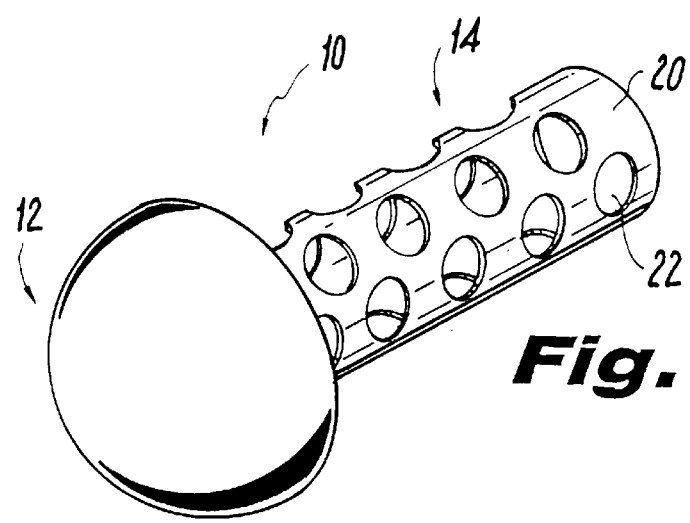
FIG. 2 is a left perspective view of the stent of FIG. 1.
Figure 3:
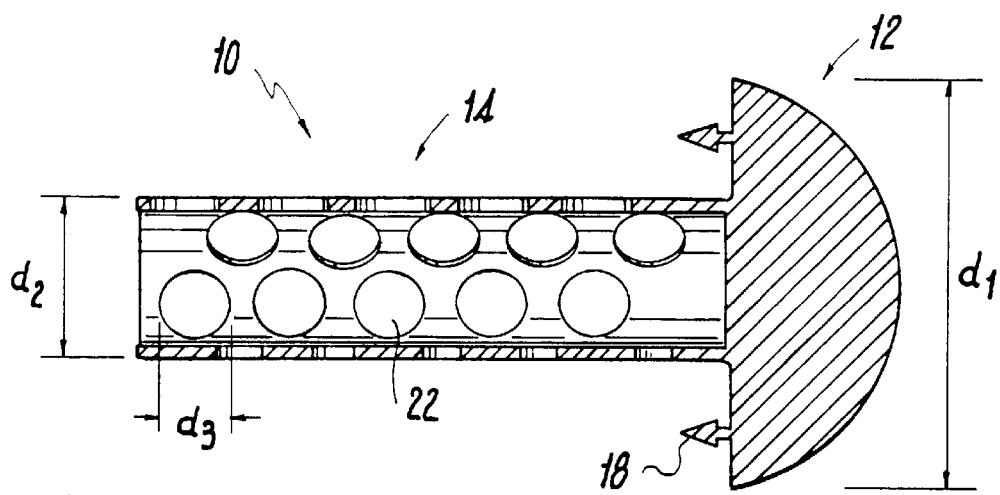
FIG. 3 is a cross-sectional view taken along line 3—3 shown in FIG. 1.

With reference to FIGS. 1–3, a preferred perfusion stent is designated generally by reference numeral 10. Perfusion stent 10 includes a head 12 and a stem 14 extending along the longitudinal axis of stent 10. The head 12 is preferably imperforate and dome-shaped. The head 12 also preferably includes at least one barb 18 for securing stent 10 to heart tissue as further discussed below. The stem portion 14 includes a cylinder 20 having a plurality of holes 22. The diameter, $d_1$, of the head portion 12 is preferably about 3 mm±2 mm, and the diameter, $d_2$, of the stem portion 14 is preferably about 2 mm±1.5 mm. The diameter, $d_3$, of a hole 24 is preferably about 2 mm±1.5 mm.

Figure 4:
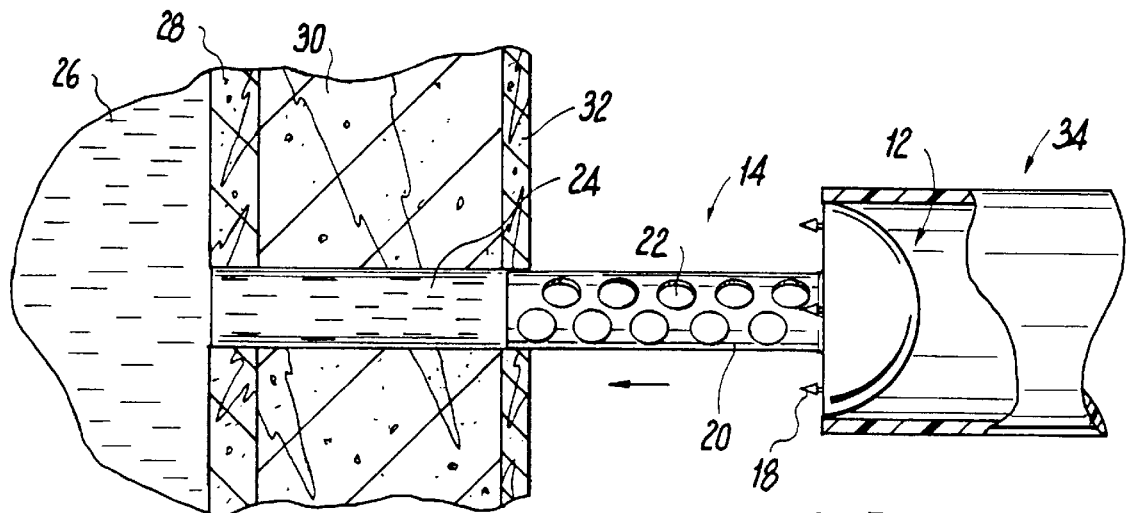
FIG. 4 is a side partial cross-sectional view of the stent being implanted within TMR channel.
Figure 5:
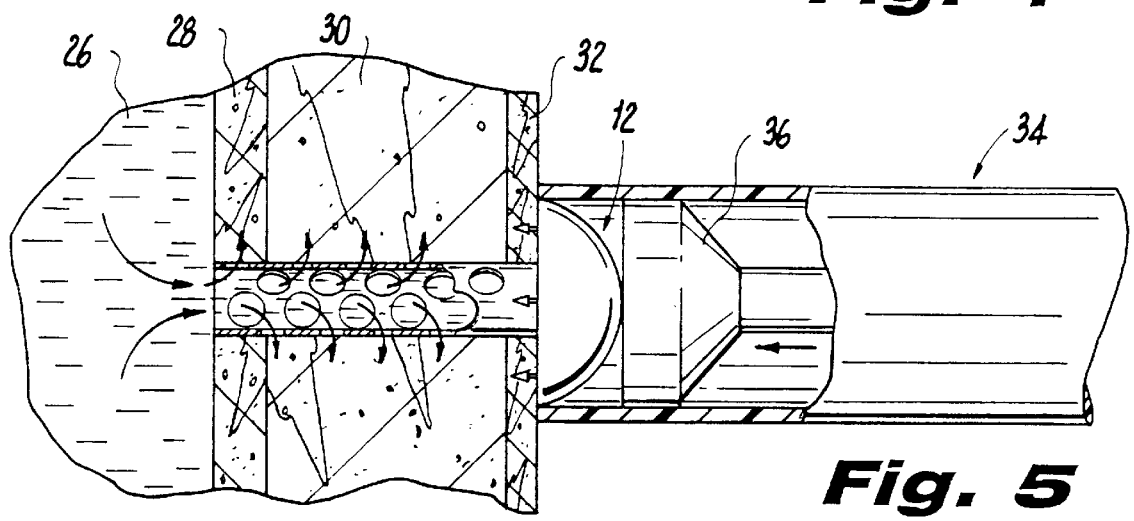
FIG. 5 is a side partial cross-sectional view of the stent implanted within the TMR channel.

Referring now to the side partial cross-sectional views of FIGS. 4–5, a preferred method of implanting perfusion stent 10 within the TMR channel is disclosed During the TMR procedure, one or more channels are formed in the heart to facilitate blood delivery to ischemic areas of the heart. The channels are formed by a channel creating device. The channel creating device may be a mechanical coring device as disclosed in U.S. patent application Ser. No. 08/650,485, filed on May 13, 1996 entitled CORING DEVICE AND METHOD, to Pacala et al., or an advancing lasing device as disclosed in U.S. patent application Ser. No. 08/648,638 filed on May 13, 1996 entitled LASING DEVICE, to Pacala et al. Channel 24, is preferably a substantially uniform diameter as shown in FIG. 4 and extends from a ventricle 26, through the endocardium 28, through the myocardium 30, to the epicardium 32.

Once channel 24 is formed, the perfusion stent 10 can be implanted within channel 24. The stent 10 can be implanted manually or by a device 34 designed to hold and release the stent 10 within the channel 24 by the aid of a pusher 36. It is also contemplated to use a endoscopic instrument having a stent holding assembly at a distal end thereof and inserting the instrument within a catheter to implant the stent 10 within an endoscopically created TMR channel. Stent 10 can be expanded, threaded or press-fitted within TMR channel 24. As shown by FIG. 5, the stent 10 is preferably secured to the heart 38 by barbs 18. Once the stent 10 is implanted within channel 24, blood can flow from ventricle 26 through cylinder 20 and to ischemic areas of the heart 38 via holes 22 as shown by the arrows in FIG. 5. Bleeding is prevented at the epicardium 32 by head 12.

Figure 6:
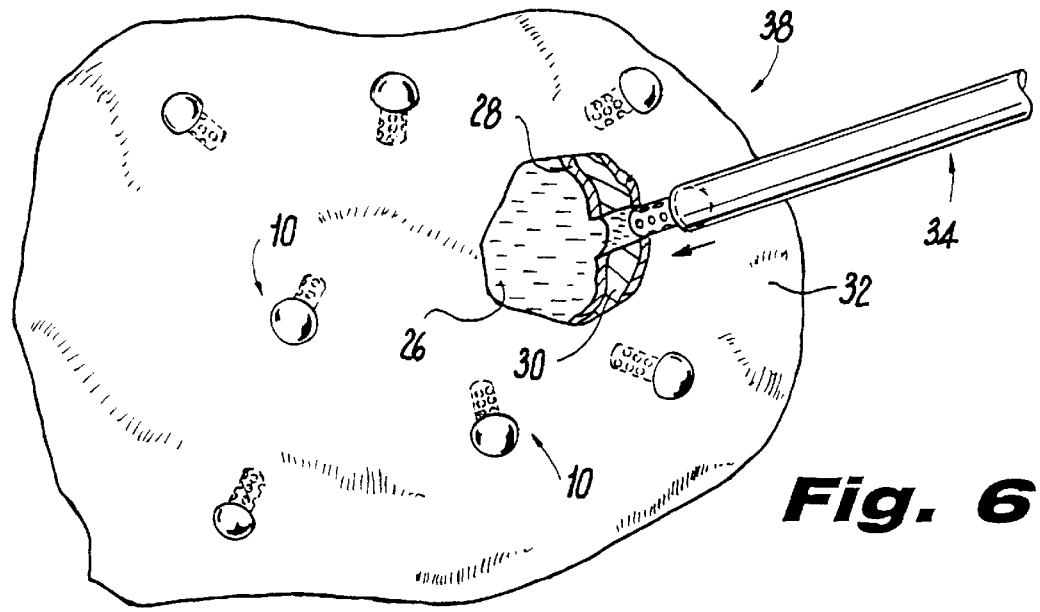
FIG. 6 is a top view of the heart having a plurality of stents implanted therein.

A top view of heart 38 having a plurality of stents 10 implanted therein is shown by FIG. 6. The number of stents 10 implanted depends on several factors, such as the duration and extent a particular area of the heart has been deprived of oxygen.

Figure 7:
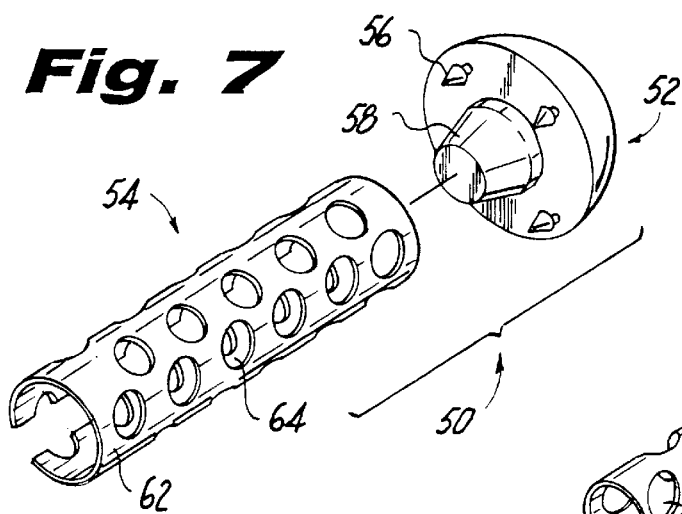
FIG. 7 is a perspective view of a perfusion stent of an alternative embodiment.
Figure 8:
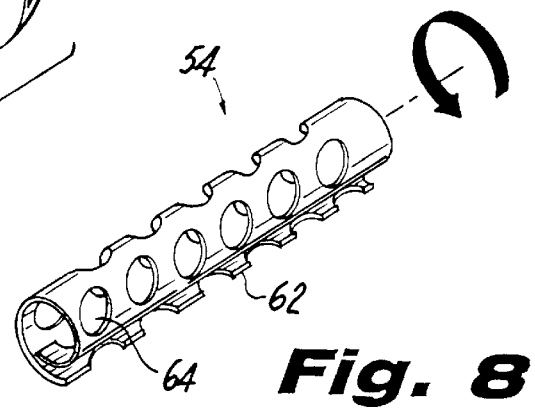
FIG. 8 is a perspective view of the stem portion of the embodiment of FIG. 7.

With reference to FIGS. 7–8, an alternative embodiment of a perfusion stent is illustrated and designated generally by reference numeral 50. Stent 50 includes head 52 and stem 54. Head 52 is dome-shaped and preferably includes at least one barb 56 for securing stent 50 to heart tissue. Head 52 further includes an attachment knob 58 for securing head 52 to stem 54 once stem 54 is within TMR channel 60. The stem portion 54 includes a metallic elongated sheet 62 having shape memory alloy for expanding in size and a plurality of holes 64 thereon. When fully expanded, as shown by FIG. 7, stem portion 54 resembles a tube having a diameter approximately equal to the largest diameter of knob 58.

Figure 9:
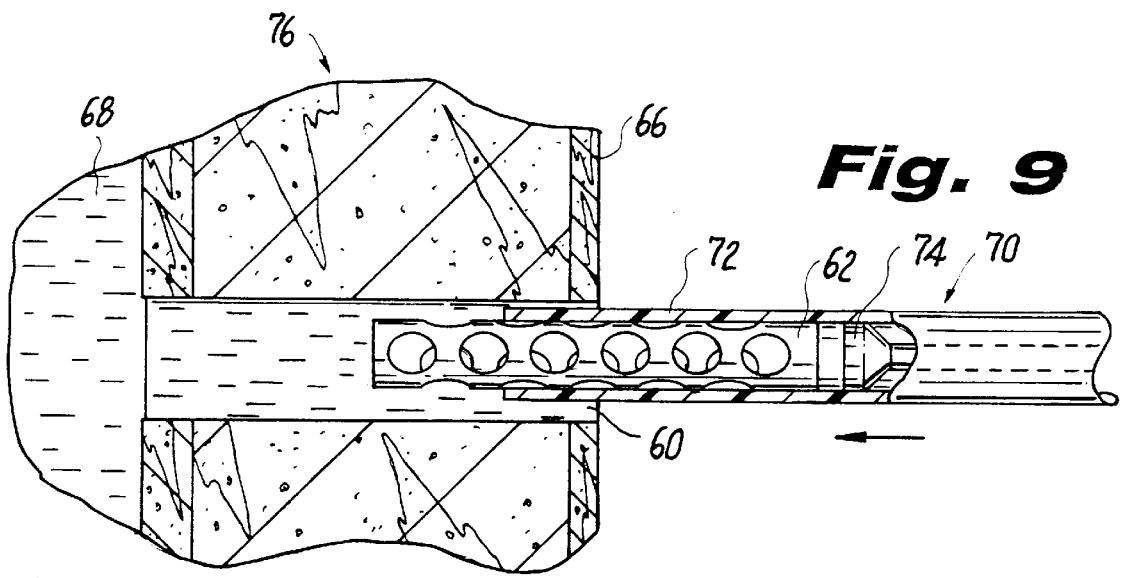
FIG. 9 is a side partial cross-sectional view of the stent of FIG. 7 being implanted within the TMR channel.

During a TMR procedure, sheet 62 is inserted within channel 60 which extends from the epicardium 66 to a ventricle 68. The sheet 62 can be manually or mechanically inserted within channel 60 with the aid of a mechanical insertion device 70 as shown by FIG. 9. Device 70 includes a tubular portion 72 designed to hold sheet 62 and a pusher 74 designed to push sheet 62 within channel 60.

When sheet 62 is inserted within channel 60, the shape memory alloy expands causing sheet 62 to assume a tube-like shape and therefore be frictionally secured to the heart tissue. The shape memory alloy can be expanded due to sensing an increase in temperature brought about by moving the sheet 62 from room temperature to body temperature. The diameter, $d_4$, of the sheet 62 in the fully expanded configuration is approximately 2 mm±1.5 mm. Knob 58 of head 52 can then be inserted within stem 54 to attach head 52 to stem 54. The barbs 56 on head 52 are used to secure head 52 to the heart 76. In an alternative embodiment as shown by FIG. 10A, head 52 may be secured to stem 54 by press-fitting alone.

Figure 10:
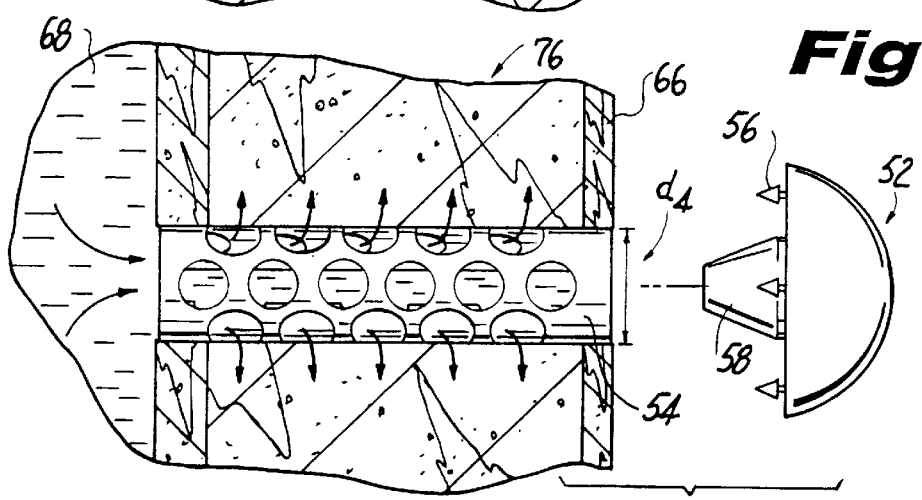
FIG. 10 is a side partial cross-sectional view of the stent of FIG. 7 being implanted within the TMR channel.
Figure 10A:
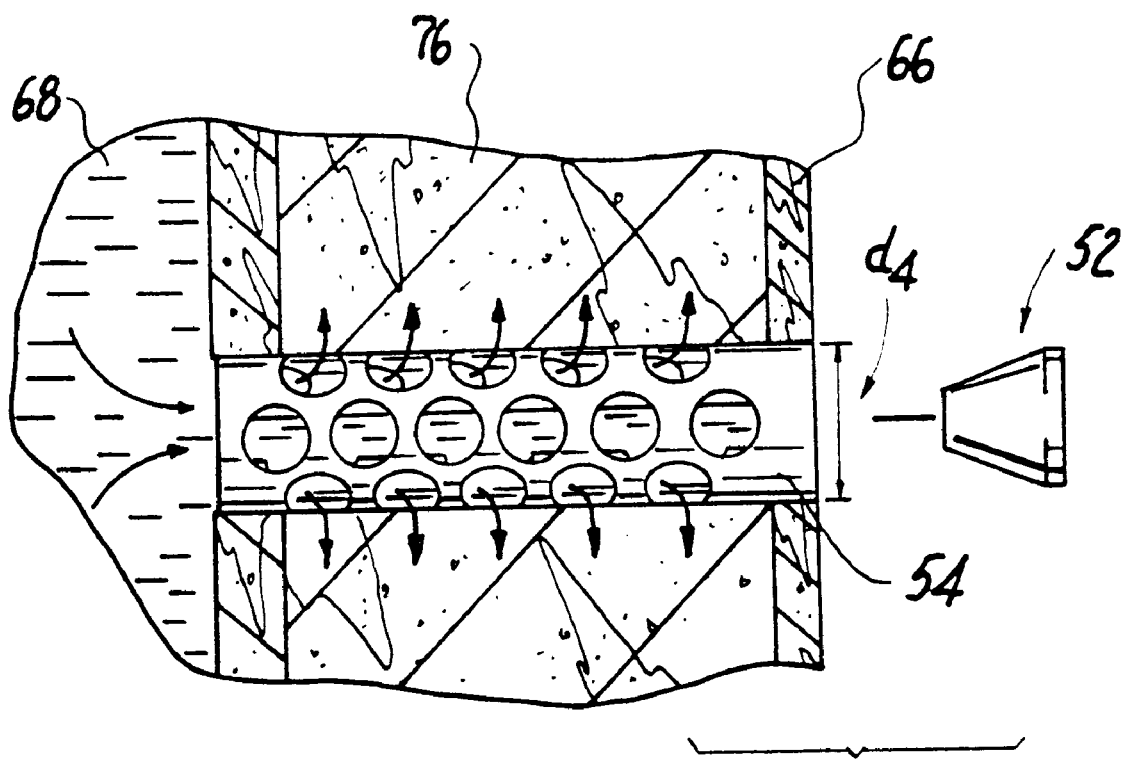
FIG. 10A is a side partial cross-sectional view of an alternative embodiment Of the stent implanted within the TMR channel.

As shown by FIG. 10, stent 50, when implanted within channel 60, is in fluid connection with ventricle 68. This permits blood to flow from the ventricle 68, through stem 54 and to the ischemic areas of the heart 76 as shown by the arrows in FIG. 10. Additionally, stent 50 enables the channel 60 to remain patent in the long term and prevents bleeding from the epicardium 66.

It will be understood that various modifications can be made to the embodiment disclosed herein. Therefore, the above description should not be construed as limiting, but merely as exemplifications of preferred embodiments. Those skilled in the art will envision other modifications within the scope and spirit of the claims appended hereto.

What is claimed is:

1. A method for performing transmyocardial revascularization (TMR) comprising the steps of:

providing a perfusion stent which includes a cylindrical stem having a proximal end, a distal end and an intermediate portion therebetween defining a stem wall, said intermediate portion having a plurality of holes in fluid communication with an internal cavity bound by the intermediate portion, said intermediate portion defining an outer diameter which is substantially equal to an outer diameter defined by the distal end, said stem wall having a substantially straight profile from the proximal end to the distal end;

creating a channel in the heart tissue by advancing a channel creating device into the myocardium to a ventricle; and implanting said perfusion stent in the channel, said internal cavity being in fluid communication with blood flow in the ventricle to deliver blood from the ventricle through the internal cavity and to the heart tissue via said plurality of holes.

2. The method according to claim 1, wherein said stem is formed of shape memory alloy and the method includes the step of expanding the stem when said stent is implanted within said channel to secure said stent to the heart tissue.

3. The method according to claim 1, wherein said step of implanting said stent within said channel is performed manually.

4. The method according to claim 1, wherein said steps of providing and implanting said stent is performed by a device having an assembly for holding and releasing said stent within said channel.

5. The method according to claim 1, wherein said step of creating a channel in the heart tissue is performed by laser ablation device.

6. A perfusion stent comprising:

a tubular member having a plurality of holes, said member configured for implantation within a channel to extend from a ventricle into the heart tissue; and a head member removably attached to said tubular member for closing an end of said tubular member.

7. The perfusion stent according to claim 6, wherein said tubular member includes shape memory alloy which expands when said stent is implanted within channel to secure said stent to the heart tissue.

8. The perfusion stent according to claim 6, wherein said head member has at least one fastener for securing said stent to the heart wall.

9. The perfusion stent according to claim 6, wherein said head member is dome-shaped.

10. The perfusion stent according to claim 7, wherein said tubular member has a diameter of about 0.5 mm to about 3.5 mm when expanded.

11. The perfusion stent according to claim 6, wherein said head member includes an extension for being press-fitted to said tubular member for attaching said head member to said tubular member.

12. A perfusion stent comprising:

a tubular member having a plurality of holes, said member formed of shape memory alloy which is expandable when said stent is implanted within a channel in heart tissue to secure the stent to the heart tissue; and a head member removably attached to said tubular member for closing an end of said tubular member.

13. The perfusion stent according to claim 12, wherein said tubular member has a diameter of about 0.5 mm to about 3.5 mm when expanded.

* * * * *